(12) United States Patent
Kosterev

(10) Patent No.: US 7,805,980 B2
(45) Date of Patent: Oct. 5, 2010

(54) SELECTIVITY ENHANCEMENT IN PHOTOACOUSTIC GAS ANALYSIS VIA PHASE-SENSITIVE DETECTION AT HIGH MODULATION FREQUENCY

(75) Inventor: Anatoliy Kosterev, Houston, TX (US)

(73) Assignee: William Marsh Rice University, Houston, TX (US)

( * ) Notice: Subject to any disclaimer, the term of this patent is extended or adjusted under 35 U.S.C. 154(b) by 693 days.

(21) Appl. No.: 10/597,844

(22) PCT Filed: Feb. 9, 2005

(86) PCT No.: PCT/US2005/004125

§ 371 (c)(1),
(2), (4) Date: Jul. 10, 2007

(87) PCT Pub. No.: WO2005/077061

PCT Pub. Date: Aug. 25, 2005

(65) Prior Publication Data

US 2008/0127715 A1 Jun. 5, 2008

Related U.S. Application Data

(60) Provisional application No. 60/542,944, filed on Feb. 9, 2004.

(51) Int. Cl.
*G01N 21/00* (2006.01)
(52) U.S. Cl. ....................................... 73/24.02
(58) Field of Classification Search ....................... None
See application file for complete search history.

(56) References Cited

U.S. PATENT DOCUMENTS

| 4,738,536 | A |   | 4/1988  | Kitamori et al. |
|-----------|---|---|---------|-----------------|
| 5,159,411 | A | * | 10/1992 | Hammerich et al. ......... 356/432 |
| 6,608,683 | B1| * | 8/2003  | Pilgrim et al. ............... 356/432 |

OTHER PUBLICATIONS

A. A. Kosterev, et al.; Photoacoustic Phase Shift as a Chemically Selective Spectroscopic Parameter; Applied Physics B; 2004; vol. 78, pp. 673-676; Rice University USA.
International Search Report for PCT/US05/004125 dated Jun. 2, 2006.

* cited by examiner

*Primary Examiner*—Hezron Williams
*Assistant Examiner*—Mark Shabman
(74) *Attorney, Agent, or Firm*—Conley Rose, P.C.; Rodney B. Carroll

(57) ABSTRACT

A method for detecting a target fluid in a fluid sample comprising a first fluid and the target fluid using photoacoustic spectroscopy (PAS), comprises a) providing a light source configured to introduce an optical signal having at least one wavelength into the fluid sample; b) modulating the optical signal at a desired modulation frequency such that the optical signal generates an acoustic signal in the fluid sample; c) measuring the acoustic signal in a resonant acoustic detector; and d) using the phase of the acoustic signal to detect the presence of the target fluid.

19 Claims, 4 Drawing Sheets

US 7,805,980 B2

SELECTIVITY ENHANCEMENT IN PHOTOACOUSTIC GAS ANALYSIS VIA PHASE-SENSITIVE DETECTION AT HIGH MODULATION FREQUENCY

STATEMENT REGARDING FEDERALLY SPONSORED RESEARCH OR DEVELOPMENT

This invention was made with government support under grant number NAG9-01482 awarded by the NASA Johnson Space Center. The government has certain rights in the invention.

TECHNICAL FIELD OF THE INVENTION

The present invention provides a new spectroscopic method for distinguishing molecular species having overlapping absorption spectra using photoacoustic spectroscopy.

BACKGROUND OF THE INVENTION

Photoacoustic spectroscopy (PAS) is an analytical method that involves stimulating a sample with modulated light and detecting the resulting sound waves emanating from the sample. A photoacoustic measurement can be made as follows. First, light is used to stimulate molecules within a sample. Such stimulation can include, for example, absorption of the light by the molecule to change an energy state of the molecule. As a result, the stimulated molecule enters an excited state. Optical excitation is followed by the energy transfer processes (relaxation) from the initially excited molecular energy level to other degrees of freedom, in particular translational motion of the fluid molecules. During such relaxation, heat, light, volume changes and other forms of energy can dissipate into the environment surrounding the molecule. Such forms of energy cause expansion or contraction of materials within the environment. As the materials expand or contract, sound waves are generated.

In order to produce identifiable sound waves, or photoacoustic signals, the light is pulsed or modulated at a specific resonant acoustic or modulation frequency f (having a modulation period 1/f), sometimes also referred to herein as ω. The sample environment can be enclosed and may be constructed to resonate at the modulation frequency. An acoustic detector mounted in acoustic communication with the sample environment can detect changes occurring as a result of the modulated light stimulation of the sample. Because the amount of absorbed energy is proportional to the concentration of the absorbing molecules, the acoustic signal can be used for concentration measurements.

In typical PAS, a resonant acoustic cavity or sample cell with a quality factor Q is used to isolate and amplify sound wave signals, thereby increasing sensitivity of detection. The light intensity or wavelength is modulated at f. The absorbed energy is accumulated in the acoustic mode of the sample cell during Q oscillation periods. Hence, the acoustic signal is proportional to the effective integration or energy accumulation time t, where $t=Q/f$. Most often the Q factor is in the range 40-200 and f=1,000-4,000 Hz. Thus, for example, Q may equal 70 and f=1250 Hz, with the result that t=0.056 s.

Typically, only a narrow range of wavelengths of light is introduced into a sample. Such narrow range of wavelengths can be formed by, for example, a laser. Utilization of only a narrow range of wavelengths can enable pre-selected molecular transitions to be selectively stimulated and studied. In some instances the species of interest may have an absorption spectrum that is sufficiently distinct that a meaningful measurement can be made simple by carrying out PAS at that wavelength.

In other instances, however, such as when the sample contains more than one molecular species with overlapping absorption spectra, it is difficult or even impossible to measure or detect the presence of one of the species using PAS. When the two (or more) spectra are overlaid, there is no way to identify the spectrum attributable to each species in the resulting spectrum. Hence, it is desirable to provide a PAS technique that will allow distinction between gaseous species in a multi-component mixture even when their absorption spectra overlap.

SUMMARY OF THE INVENTION

The present invention allows distinction between gaseous species in a multi-component mixture even when their absorption spectra overlap. The present system uses a high modulation frequency so that the phase lag attributable to each species becomes apparent. Because different species have different phase lags, the phase lag may be used as a distinguishing factor between interfering photoacoustic signals.

In one embodiment of the present invention, the measured acoustic signal is rotated in phase so as to suppress the signal generated by the interfering species and thereby allow detection of a signal from the target species. In some embodiments, the system is used to detect small amounts of one fluid, the target fluid or "impurity," in a large quantity of a primary species, the "background" species. Either the primary species or the impurity may comprise more than one chemical species. In other embodiments the phase rotation is used to suppress the signal from the interfering species so that small signals resulting from the target fluid or impurity can be measured with great precision. Alternatively, the system can be used to monitor relative amounts of two fluids in a fluid sample or stream.

BRIEF DESCRIPTION OF THE DRAWINGS

For a more detailed understanding of the invention, reference will be made to the accompanying Figures, in which.

DETAILED DESCRIPTION OF THE PREFERRED EMBODIMENTS

Apparatus

Figure 1:
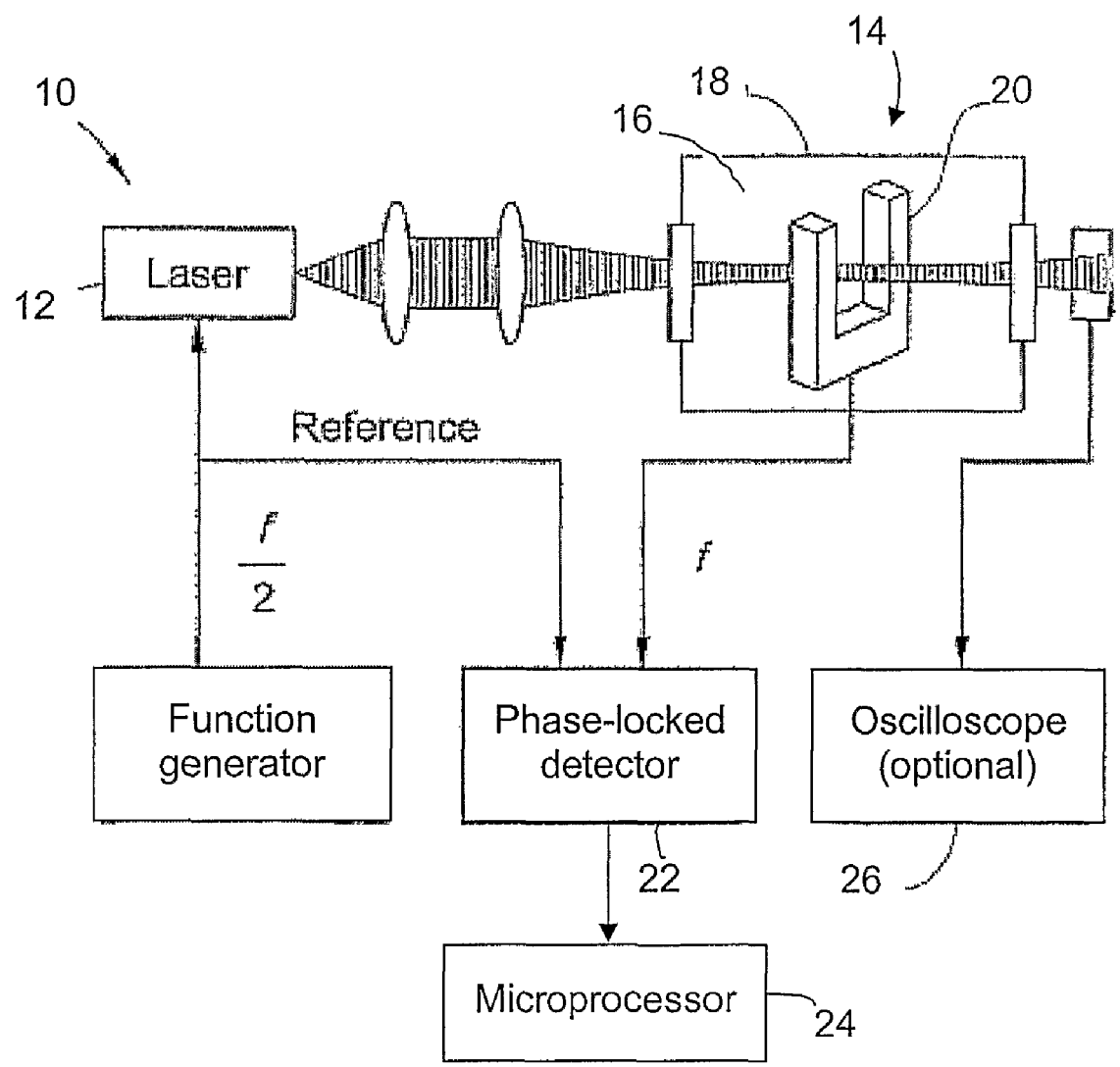
FIG. 1 is a schematic drawing of a system constructed in accordance with one embodiment of the invention.

To carry out the present invention, a photoacoustic spectroscopy cell is configured to apply a modulated light signal to a sample and to detect the resulting acoustic signal using a phase-locked detector. By way of example, reference is made to FIG. 1, in which a photoacoustic apparatus 10 comprises a light source 12 configured to emit a beam of radiation into a sample holder 14. Light source 12 can comprise, for example, a laser. Filters (not shown) may be provided between light source 12 and sample holder 14 if desired.

Sample holder 14 includes a sample cell 18 containing a sample 16. Sample cell 18 can comprise a number of materials known to persons of ordinary skill in the art, and preferably comprises a material substantially transparent to the wavelength(s) of light emanating from light source 12. Preferred materials for sample cell 18 will accordingly vary depending on the wavelengths of light utilized in the spectroscopic apparatus.

Sample 16 may be a fluid or a gas and may substantially fill sample cell 18. Sample 16 can, for example, comprise a gas stream in which it is desired to detect the presence of a contaminant gas or impurity.

Apparatus 10 further comprises an acoustic detector 20 mounted to sample cell 18 and in acoustic communication with sample 16. Acoustic detector 20 preferably comprises a transducer such as, for example, a piezoelectric element or a microphone and is mounted such that a fluid is provided between a surface of detector 20 and sample cell 18. In the embodiment shown, acoustic detector 20 comprises quartz tuning fork. In alternative embodiments (not shown), acoustic detector 20 can be another type of detector and may be mounted on the inside or outside wall of sample cell 18. Detector 20 is typically removably mounted to sample cell 18 by, for example, a clamp. Acoustic detector 20 is in electrical communication with a phase locked detector 22, which is preferably in electrical communication with a microprocessor 24. In certain embodiments, microprocessor 24 processes the incoming signal as described in detail below.

An optional output device 26 may be included and can be configured to facilitate alignment of the through beam. Output device 22 can comprise, for example, an oscilloscope, or any other suitable device.

Operation

In operation, a beam of light is generated by light source 12 according to a signal from a function generator and is passed through sample cell 18 to stimulate molecular excitation within sample 16. The function generator also provides a reference electrical signal such as a sine or rectangular wave synchronized to the laser light modulation. Nonradiative decay or molecular rearrangements cause expansions and/or contractions of a material within sample 16 to generate acoustic waves passing from sample 16 to acoustic detector 20. Acoustic detector 20 detects the resulting acoustic waves and passes signals corresponding to, for example, gas pressure changes in the acoustic waves to phase-locked detector 22. Phase-locked detector 22 produces two outputs (DC voltage levels, X and Y) corresponding to in-phase and quadrature components of the acoustic detector signal with respect to the reference signal. Output device 22 can be configured to convert information obtained from phase-locked detector to, for example, a graphical or numerical display.

In some embodiments, the system can be programmed to utilize known phase angles (rotations) that have been generated empirically by measuring the phase angle of each known component (or mixture) separately.

Signal Processing

Figure 2A:
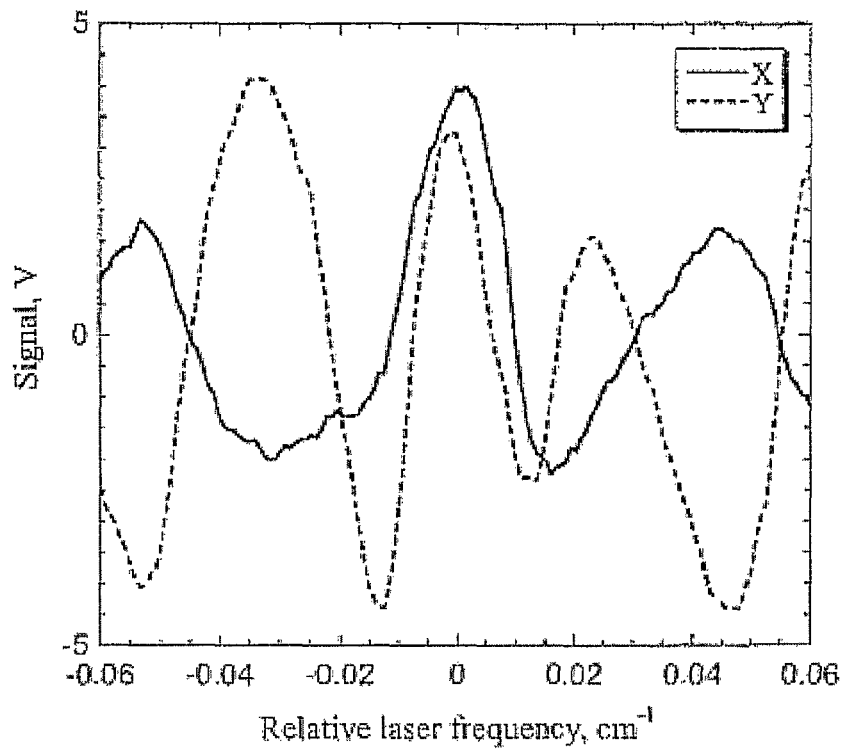
FIGS. 2A and 2B are plots illustrating the change in signal output when the signal is processed according to the present invention.
Figure 3A:
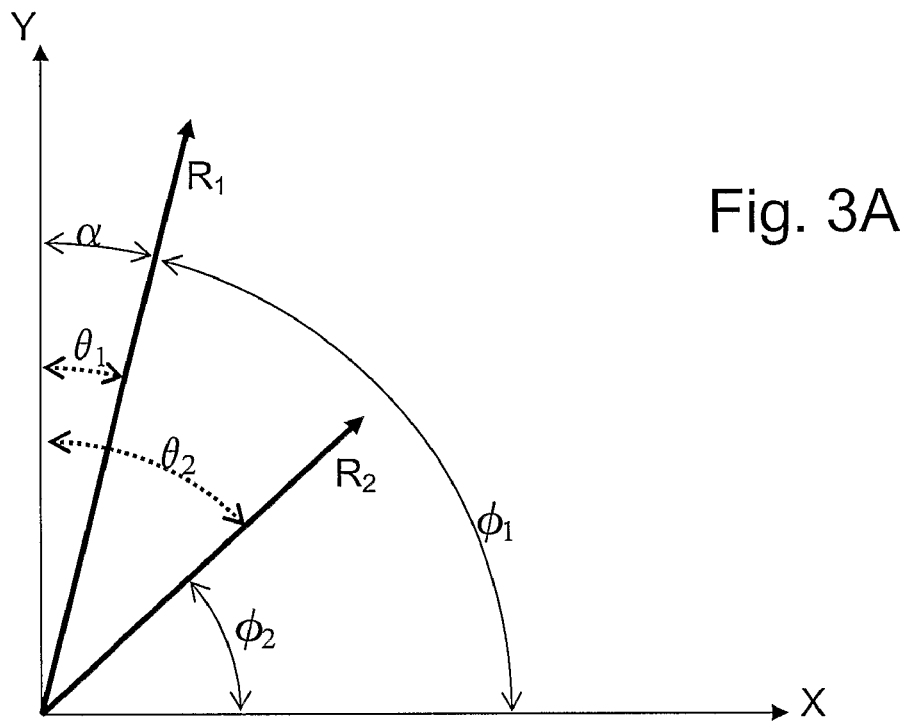
FIGS. 3A-3C are plots illustrating the principles applied in the present invention.

When the gas sample is a two-component gas, the resulting signal might resemble the spectrum of FIG. 2A. In FIG. 2A the horizontal axis gives the relative laser frequency, the vertical axis gives the signal strength and the two plots are the X and Y components ("in-phase and quadrature components") of the signal produced by the multi-component system. Referring briefly to FIG. 3A, the signal is illustrated as a plot of two vectors in the complex plane, $R_1$ and $R_2$, which each represents the phase-delayed photoacoustic response of one of the two gas species. In FIG. 3A, the phase lag for each component is indicated by $\theta$. Projections of these vectors to the x- and y-axes are the experimentally observed in-phase and quadrature components when the lock-in amplifier phase is referenced to the laser driver modulation input. The X and Y plots in FIG. 2A are the x- and y-components of the sum of these signals (vectors) as a function of frequency.

Figure 2B:
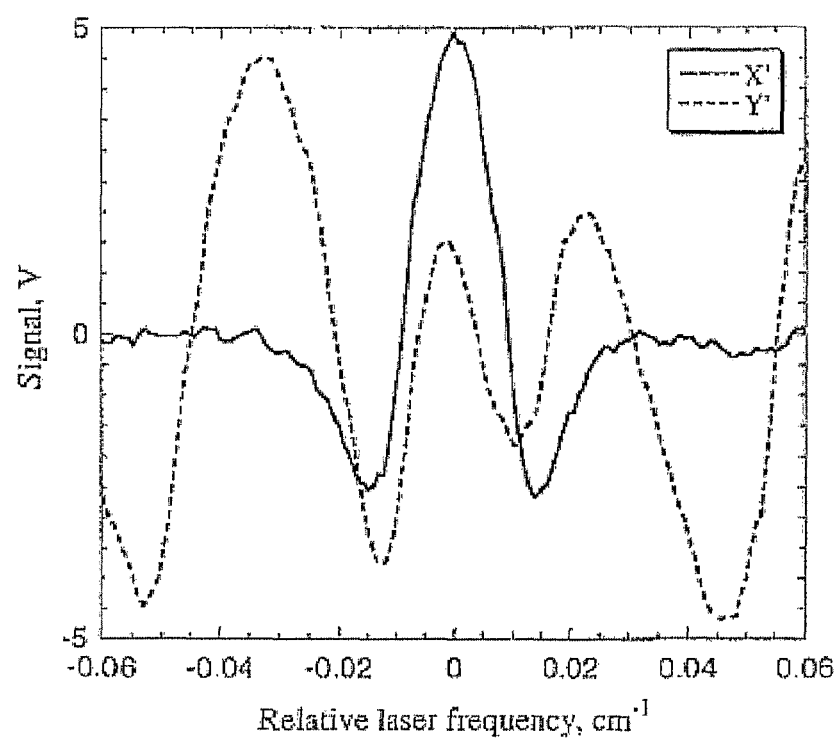
Figure 3B:
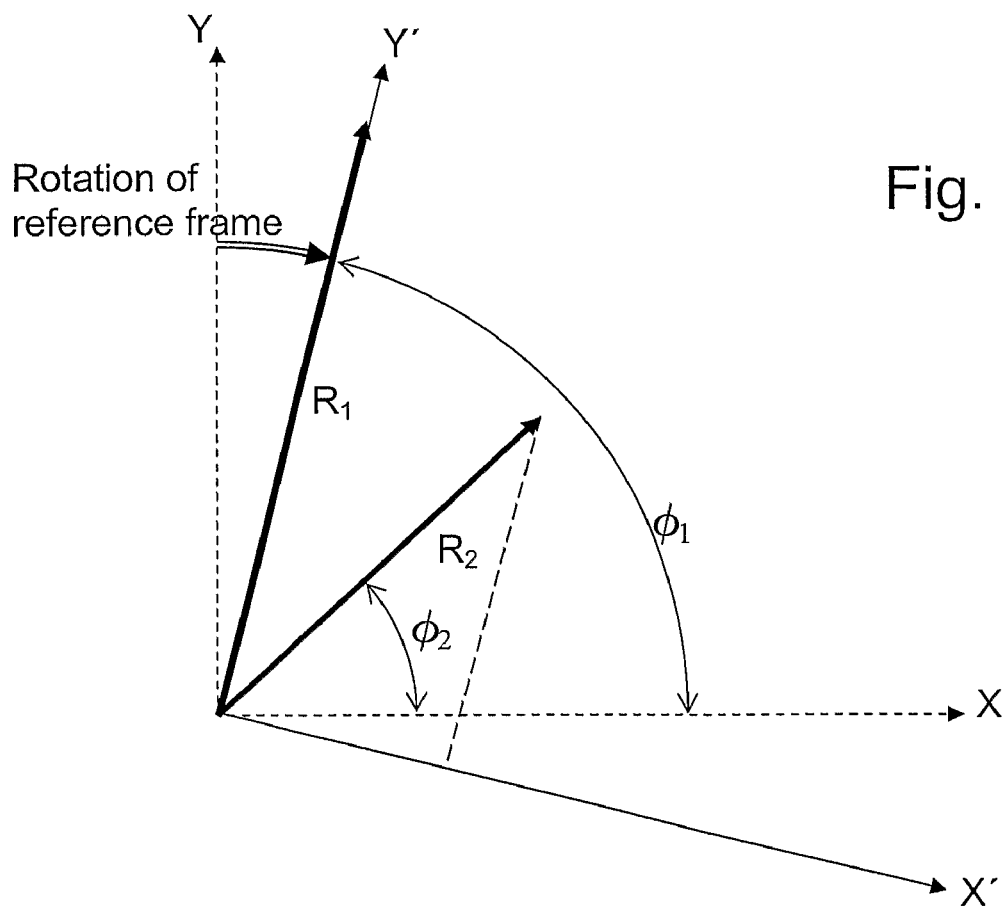

The phase lag (angle) $\theta$ of each component is shown in FIG. 3A. If the reference frame of the system is rotated by $\alpha$ degrees, where $\alpha=\theta_1$, such that the new x-axis is orthogonal to vector $R_1$ as shown in FIG. 3B, the corresponding quadrature component (X') will comprise only $R_2$. This is illustrated in FIG. 3A, where $\alpha$ is shown, and in FIG. 3B, in which the axes have been rotated until the vector $R_1$ lies on the y-axis. When the signal is processed in this manner and input from the component of interest ($R_2$) is detectable, the X' component clearly indicates an optical absorption line at the resonance frequency of the component of interest, as illustrated in FIG. 2B. Thus, by using phase lag to calculate a rotated reference frame, a quadrature component can be generated that gives selective information about the presence (or absence) of a specific species.

As an alternative to using two receivers, a single receiver with an adjustable phase may be employed. If desired, the receiver phase may be pre-set to receive a signal that is in quadrature to the photoacoustic signal from the interfering species, i.e., set to receive x' as derived above. The phase rotation angles are preferably determined experimentally for each pair of components, as well as optimum pressure and modulation conditions.

Rotation of Reference Frame

In one implementation, the acoustic signal is measured by an in-phase receiver and a quadrature-phase receiver that are both phase-locked to the modulation of the optical signal. The in-phase signal amplitude and the quadrature phase signal amplitude together represent the x,y coordinates of a vector that forms an angle $\theta$ with the x-axis ($\theta$ represents the phase lag) and has a magnitude representing the amplitude of the photoacoustic signal. The two species are measured independently to determine the phase lag for each, call them $\theta_1$ and $\theta_2$. The coordinates of a photoacoustic signal from a mixture of the two species will be a vector sum of the two acoustic signals. This could be written:

$$X=x_1+x_2=A_1\cos\theta_1+A_2\cos\theta_2$$

$$Y=y_1+y_2=A_1\sin\theta_1+A_2\sin\theta_2$$

A rotation of the vector by one of the angles (say $-\theta_1$) will result in a suppression of one of the signals along the y-axis. A phase rotation may be expressed:

$$X'=x\cos(-\theta_1)-y\sin(-\theta_1)$$

$$Y'=x\sin(-\theta_1)+y\cos(-\theta_1)$$

Algebraic manipulation of the foregoing equations, and use of some trigonometric identities, yields:

$$X'=A_1+A_2\cos(\theta_2-\theta_1)$$

$$Y'=A_2\sin(\theta_2-\theta_1)$$

Note that Y' reflects only the amount of species 2, and is independent of any contribution from species 1.

Instrument Lag

Figure 3C:
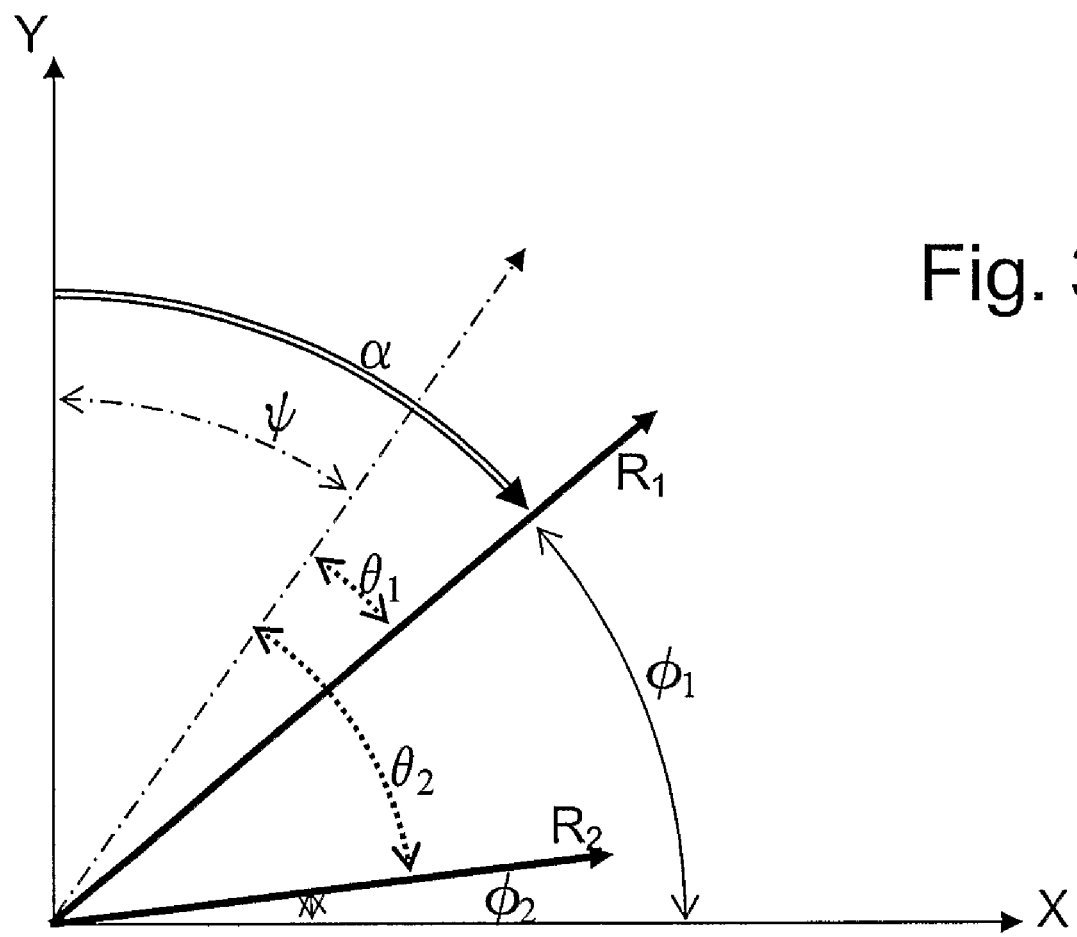

In actual operation, the system used to carry out the invention will have its own inherent phase lag. This lag, the instrument lag, manifests itself as a further lag on the measured signal, as indicated by $\psi$ in FIG. 3C. The instrument lag $\psi$ can be measured empirically or can be treated as part of the phase lag for the background component. Regardless, the reference frame of the signal is rotated until it is orthogonal to the signal from one component (the background component), so that a quadrature signal for the component of interest can be detected.

As described above, the present invention is based on the use of phase lag, $\theta$, for at least one component. An observable phase lag can only be achieved if the modulation period of the optical energy absorption is comparable to or shorter than the V-T relaxation time $\tau$. Therefore it is preferred that the modulation frequency $\omega$ be greater than $1/\tau (\omega \geqq 1/\pi)$. Preferred frequencies are at least 5,000 Hz, more preferably at least 10 kHz, and still more preferably at least 30 kHz. Further, it has been found that the present phase-selective approach works very well with a recently introduced quartz-enhanced photoacoustic spectroscopy (QEPAS) technique, where the modulation frequency is ~32,760 Hz. (See, A. A. Kosterev, Yu. A. Bakhirkin, R. F. Curl, and F. K. Tittel, "Quartz-enhanced photoacoustic spectroscopy," Optics Letters 27, 1902-1904 (2002)).

By way of experiment, the novel approach of the present invention was used in combination with QEPAS for the detection of CO in propylene. Regardless of the strong structured broadband background of propylene (its signal is about as strong as 3 ppmv of CO would produce), it was found that a photoacoustic signal recorded with the properly chosen phase is free from propylene interference and allows CO detection at the ~10 ppbv level or better.

Thus, it has been demonstrated that the present invention is useful for spectroscopic detection and quantification of concentrations of a chemical species in the presence of another species with an overlapping absorption spectrum. The experiment described above corresponds to an industrial application in which it is desired to measure trace concentrations of CO in propylene that is used in the manufacture of plastics by the petrochemical industry. It is further envisioned that the principles described herein can be applied and used to detect impurities or additives in any single- or multi-chemical stream having a known phase lag, as the impurities or additives will appear as a shift in the phase-locked base signal.

Unlike traditional PAS, in which the optical modulation period is much longer than the relaxation rate, the present approach allows separation of different chemical species based on their relaxation rate difference, even if their optical spectra are strongly overlapping. The present invention can be applied to gaseous or liquid fluid streams or samples.

The present application incorporates by reference the disclosure of commonly owned PCT Application Number WO03104767. This research was funded in whole or in part by National Aeronautic and Space Administration-Johnson Space Center Grant Number NAG9-01482.

While the present invention has been disclosed and described in terms of preferred embodiments, the invention is not limited to the preferred embodiments. For example, the magnitude and phase lag of the signal from each component can vary significantly from the those depicted in the Figures. Likewise, the phase lags for the instrument and target and background fluids can be calibrated empirically, experimentally, or using predetermined values and the selection of a quadrature component for the detection of species may be made on any basis. Either the sample cell 18 or the acoustic transducer 20 or none of them can be resonant at the laser modulation frequency f/2, or at twice that frequency f. In addition, any recitation of steps in the claims that follow is not intended as a requirement that the steps be performed sequentially, or that one step be completed before another step is begun, unless explicitly so stated.

What is claimed is:

1. A method for detecting a target fluid in a fluid sample comprising a first fluid and the target fluid using photoacoustic spectroscopy (PAS), the method comprising:
    a) providing a light source configured to introduce an optical signal having at least one wavelength into the fluid sample;
    b) modulating the optical signal at a desired modulation frequency such that the optical signal generates an acoustic signal in the fluid sample, wherein the desired modulation frequency is greater than the relaxation rate of at least one of the first and target fluids;
    c) measuring the acoustic signal with an acoustic transducer; and
    d) using the phase of the acoustic signal to detect the presence of the target fluid.

2. The method of claim 1 wherein step c) includes performing a rotation transformation using a phase rotation angle so as to determine signal contributions from the target fluid.

3. The method according to claim 2, further including selecting an optimum phase rotation angle.

4. The method of claim 1 wherein step c) includes rotating the phase of the acoustic signal so as to suppress signal contributions of the first fluid.

5. The method of claim 4 wherein the received acoustic signal is rotated by an amount equal to the sum of the instrument phase lag and the phase lag of the first fluid.

6. The method according to claim 1 wherein step c) is carried out using an adjustable reference frame.

7. The method according to claim 5 wherein step c) includes pre-setting the adjustable reference frame to a predetermined value.

8. The method according to claim 1 wherein step c) is carried out using an in-phase receiver and a quadrature-phase receiver that are each phase-locked to the modulation of the optical signal.

9. The method according to claim 1 wherein step c) is carried out using a single receiver having an adjustable phase.

10. The method according to claim 1 wherein the optical signal in step (a) comprises light having a wavelength selected such that the target fluid resonates at that wavelength.

11. The method according to claim 1 wherein the modulation frequency is greater than 30 kHz.

12. The method according to claim 1, further including the step of optimizing the difference in phase lag between the first and target fluids by optimizing the modulation frequency.

13. An apparatus for detecting a target fluid in a fluid stream containing a first fluid and the target fluid using photoacoustic spectroscopy (PAS), the apparatus comprising:
    a light source configured to introduce an optical signal having a wavelength into the fluid stream, said optical signal being modulated at a modulation frequency having a desired modulation frequency greater than the relaxation rate of at least one of the first and target fluids such that the optical signal generates an acoustic signal in the fluid stream, said acoustic signal having a phase shift;
    a acoustic detector for detecting said acoustic signal in at least two phases so as to obtain two output signals; and
    a microprocessor for using the phase shift of said acoustic signal to convert said two output signals into information indicative of the presence of the target fluid.

14. The apparatus of claim 13 wherein said microprocessor performs a rotation transformation using a phase rotation angle so as to determine signal contributions from the target fluid.

15. The apparatus according to claim 14 wherein said microprocessor performs a rotation transformation using an optimized phase rotation angle.

16. The apparatus according to claim 13 wherein said acoustic detector includes an adjustable reference frame.

17. The apparatus according to claim 13 wherein the wavelength of the optical signal is selected such that the target fluid resonates at that wavelength.

18. The apparatus according to claim 13 wherein the modulation frequency is greater than the inverse of the relaxation time of at least one of the first and target fluids.

19. The apparatus according to claim 13 wherein said modulation frequency is greater than 30 kHz.

* * * * *